United States Patent [19]

Salz et al.

[11] Patent Number: 4,872,462
[45] Date of Patent: Oct. 10, 1989

[54] PROPHYLACTIC APRON

[76] Inventors: Gilbert Salz, 22702 Via Rodrigo, Mission Viejo, Calif. 92692; Mark Sullivan, 24953 Paseo de Valencia, #8C, Laguna Hills, Calif. 92653

[21] Appl. No.: 195,258
[22] Filed: May 18, 1988
[51] Int. Cl.[4] .............................................. A01G 5/42
[52] U.S. Cl. ..................................... 128/842; 128/846
[58] Field of Search .................... 128/842, 844, 846; 604/346, 347, 349, 355, 357, 358, 353, 370, 350, 351, 352, 366; 128/830; 2/46-51

[56] References Cited

U.S. PATENT DOCUMENTS

| 2,445,694 | 7/1948 | Predmore | 604/351 |
|---|---|---|---|
| 2,591,783 | 4/1952 | Craddock | 604/353 |
| 3,067,336 | 1/1978 | Johnson | 604/370 X |
| 3,526,227 | 11/1970 | Appelbaum | 604/350 |
| 3,536,066 | 10/1970 | Ludwig | 128/830 |
| 4,417,146 | 11/1983 | Herbert | 2/51 X |
| 4,423,523 | 11/1984 | Bodner et al. | 2/48 X |
| 4,553,968 | 11/1985 | Komis | 604/353 X |
| 4,568,340 | 2/1986 | Giacalone | 604/353 |
| 4,610,685 | 9/1986 | Raley | 604/370 X |
| 4,664,104 | 5/1987 | Jaicks | 128/830 |

FOREIGN PATENT DOCUMENTS 643730  6/1984  Switzerland ................. 604/351

Primary Examiner—Richard J. Johnson
Assistant Examiner—Kevin G. Rooney
Attorney, Agent, or Firm—Michael Bak-Boychuk

[57] ABSTRACT

A resilient thin membrane shield of substantially rectangular planform includes a peel plied adhesive strip along its upper edge and a tapered tubular segment at its center. The walls of the tubular segment are tapered in thickness and along the axis thereof, forming a feathered edge at the end opening. The membrane, furthermore, may include enlarged section ribs and edge beads for unfolding the membrane.

2 Claims, 2 Drawing Sheets

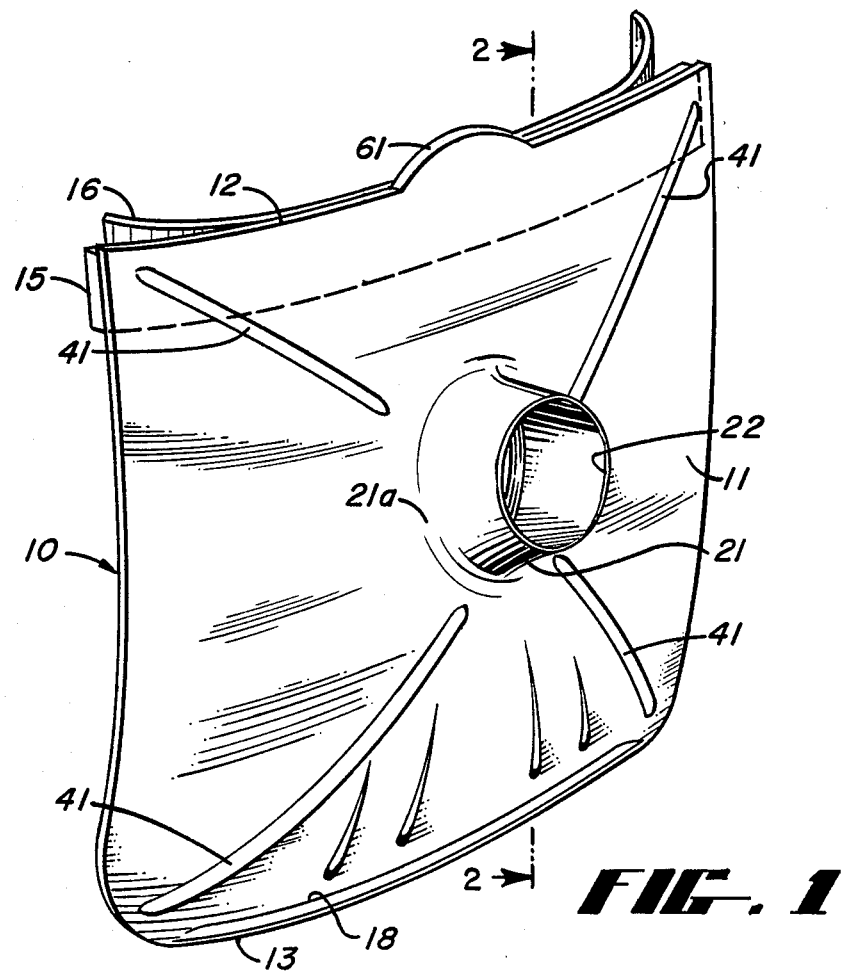
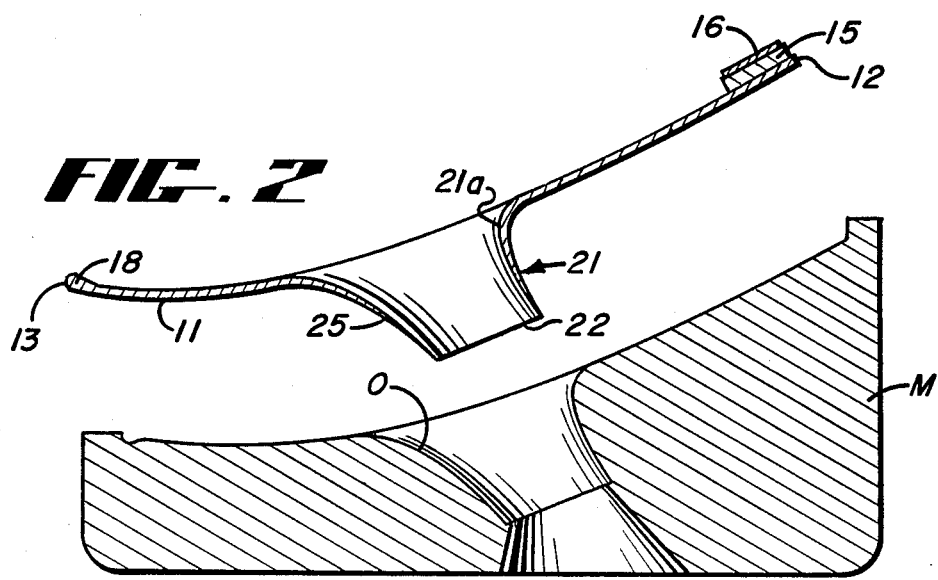

PROPHYLACTIC APRON

BACKGROUND OF THE INVENTION

1. Field of the Invention

The present invention relates to the prophylactic devices for the prevention of venereal infection, and more particularly to prophylactic shields for isolating the partners in the course of coitus.

2. Description of the Prior Art

The use of prophylactic devices for the control of disease transmission and as a barrier for birth control is well appreciated in the art. In the most prevalent form prophylactic shields or barriers are effected by way an of elastic sheath or tube closed at one end and conformed for use by the male partner in the course of sexual activity. In this form the shield extends over a portion of the male organ, while the remaining, adjacent areas are unshielded.

Recently, pernicious strains of a viral venereal disease have become significant, strains which may be transmitted by intimate contact. Thus, shielding against direct contact and the consequent exchange of body fluids has become a concern, particularly in light of the grave consequences following the infection by the AIDS virus. In the recent past, the infection rate by this last virus has reached epidemic dimensions and substantial efforts are now effected to change the sexual habits of the population at large and to improve the barrier techniques for sexual use. The epidemic aspects of this disease, however, is now of such dimensions that any deficiencies in the prior art, tolerable under prior conditions, is no longer acceptable.

Thus, convenient shields or barriers extending beyond the male genital organ are desired, particularly if conformed for practical use and distribution along with the distribution of the prophylactic device.

In the past various shielding arrangements have been devised, exemplified by, the shielding device described in the Canadian Pat. No. 1,158,507 issued to Puggard; U.S. Pat. No. 3,759,254 issued to Clark; and U.S. Pat. No. 4,664,104 issued to Jaicks. These devices, while suitable for their purposes, attend one or more particular physiological effects and thus are not directed for mass distribution. Similarly, shields for incontinence or birth control such as those described in U.S. Pat. Nos. 4,590,931 to Kidwell or 3,536,066 to Ludwig attend aspects other than those contemplated herein and thus while suitable for the purposes intended lack the convenience in fabrication and packaging necessary for wide acceptance.

Techniques and devices which provide shields useable along with a prophylactic are therefore desired and it is one such device that is disclosed herein.

SUMMARY OF THE INVENTION

Accordingly, it is the general purpose and object of the present invention to provide a resilient, elastomeric shield which is conveniently affixed to the pubic surfaces of a person.

Other objects of the invention are to provide a resilient, elastomeric, thin membrane film for use as a shield over the pubic area of the human anatomy.

Yet further objects of the invention are to provide a male public shield which is convenient in fabrication and use.

Briefly, these and other objects are accomplished within the present invention by providing a substantially rectangular thin film membrane having one edge thereof bonded to an adhesive strip plied to a cover which, once removed, then exposes the adhesive for use. Formed in the membrane subjacent the adhesive strip is a tapered, frustoconical, tubular projection comprising a peripheral wall of tapered thickness from its root to a feathered edge at its end. The opposite edge of the shield, moreover, may include a sectional enlargement of a dimension smaller than the adjacent sheet dimensions of the shield. Thus, the sectional enlargement effects a gathering of the sheet surface at its juncture for surrounding the scrotal area of the wearer.

Preferably the foregoing structure may be formed of one of the many latex based materials, with the tubular segment feathered in thickness in the course of forming. Such feathered wall thickness may be achieved by spinning the material while curing or by controlling the flow in a stationary casting.

A plurality of radially extending ribs may, furthermore, be included in the surface of the shield, extending from the foot of the tubular segment to the shield periphery. The foregoing radial ribs then provide the structural stiffness to expand any creases or folds once the shield is released from its packaging.

In this manner a discardable device is formed which may be effectively adhered to the body of the user at its upper edge and which conforms with a feathered tube segment to the male organ periphery. A prophylactic sheath may then be placed over the exterior of the tube segment, fully shielding the wearer from all sources of infection.

BRIEF DESCRIPTION OF THE DRAWINGS

FIG. 1 is a perspective illustration of the inventive shield deployed for use;

FIG. 2 is a sectional view of the shield taken along line 2—2 of FIG. 1;

DESCRIPTION OF THE SPECIFIC EMBODIMENT

Figure 3:
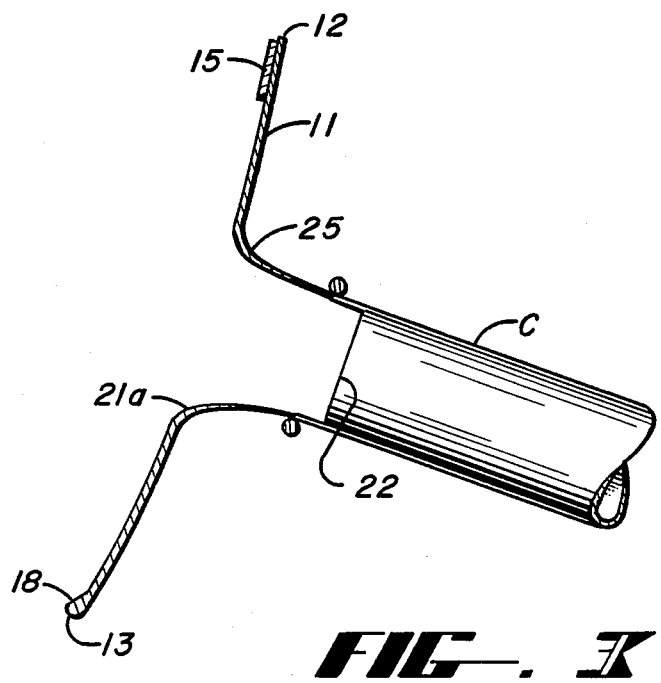
FIG. 3 is a side view section of the inventive shield engaged with a prior art device.

As shown in FIGS. 1-3 the inventive device, generally designated by the numeral 10, comprises a thin elastomeric membrane 11 of generally rectangular plan form defined by an upper edge 12 and a lower edge 13. Preferably membrane 11 may be formed of one of the many latex-based polymers and formed to a thickness of three to six mils. At the upper edge 12 membrane 11 may be faced with an adhesive strip 15 covered by a peel-ply layer 16 while the lower edge 13 may be defined by an enlarged edge bead 18. Edge bead 18 may be formed by the same polymer curing processes as those forming the remaining portions of the membrane, including processes like dipping or spraying latex into a mold with a mold alignment allowing for gravity translation towards bottom edge 13. Once thus deposited into the mold M the liquid latex is cured by the application of heat in the course of which some material shrinkage will result to evaporation. Consequently the thicker edge piece 18 will exhibit larger linear shrinkage and will thus effect a gathering at this edge of the adjacent membrane surface.

Formed substantially centrally in membrane 11, subjacent to the upper edge 12 is a frustoconical tubular projection 21 defined by a larger base or root section 21a and terminating in a smaller opening 22. Tubular projection 21 may be formed integrally with the membrane 11 by the application and gravity flow of liquid latex in the course of a downward alignment of an orifice O in a mold M. In consequence a tapered or feathered wall section is achieved along the axial direction of projection 21 wherein the edge thickness at the opening 22 is substantially less than the wall thickness.

This reduction in thickness of the wall section along the tube segment 21 effects a substantially more compliant wall at the opening 22. Thus the hoop stresses developed within the tube segment 21, i.e., its hoop compliance, will progressively increase towards the free edge. Segment 21, moreover, may be formed at a decreasing diameter taper towards its free end, converging from a faired root at 21a to the narrower feathered edge opening 22. In consequence, the constrictive hoop stresses, when worn, are minimized while a sealing engagement is effected. Preferably the axial length of segment 21 extends to a dimension of two inches or more beyond the surface of membrane 11. Thus, substantial lateral surfaces 25 are presented against which a conventional condom C may produce a seal.

The foregoing shield 10 may further include a plurality of diagonal, radially aligned ribs 41, once again, in the form of enlarged thickness strips extending from the root 21a towards the corners of membrane 11. These enlarged ribs 41 provide the necessary expansive stiffness to unfold any wrinkles or creases in the membrane acquired during packaging and storage.

Figure 4:
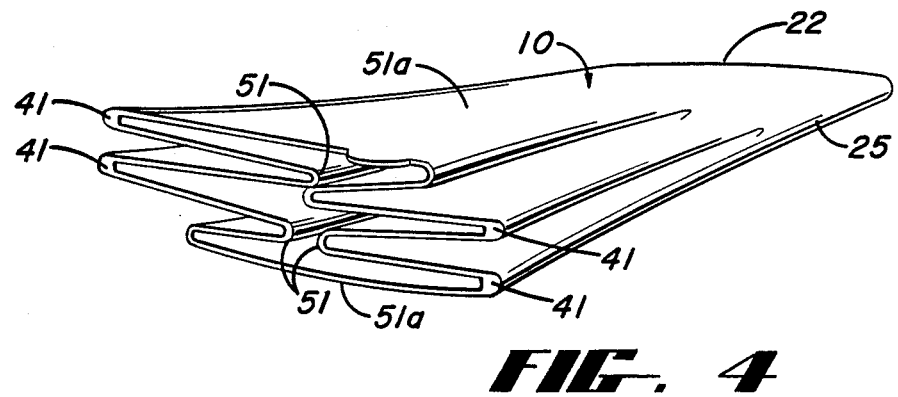
FIG. 4 is a perspective illustration of the inventive shield aligned for folding.
Figure 5:
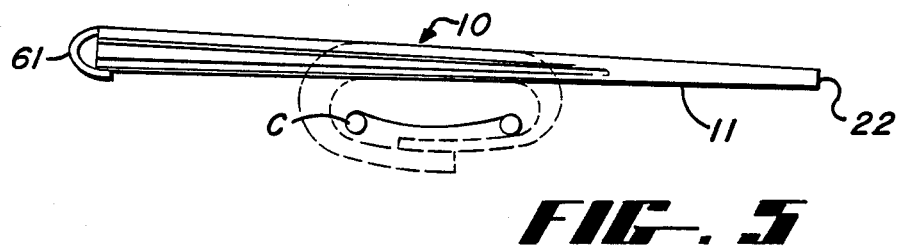
FIG. 5 is a side view, in partial section, of the inventive shield in its packaged configuration.

To effect storage membrane 11 may be folded along fold lines 51 between the ribs into overlapping fold panels 51a extending from root 21a. As thus folded a substantially rectangular planform is obtained with the folded feathered edge 22 at one end. This elongate folded form may then be wrapped around the exterior of the collapsed condom C, illustrated in FIGS. 4 and 5, thereby forming an encasement therefor when packaged. In this form a tab 61 formed in the adhesive strip 15 and extending beyond the peel ply layer 16 extends to provide an adhesive surface holding the encasing alignment together.

In consequence, the user must first release the folded shield 10 while unpacking the prophylactic condom. This fixes the sequence encouraging the use of the shield along with the condom.

The sequence of positioning may be varied from that shown in FIG. 3. For example, the shield 11 may be placed for use after the condom C is applied (not shown). This sequence is particularly effective with lubricated condoms.

In this form an inexpensive, simply packaged and conveniently stored shield is provided which may be sold along with prophylactics and which may be selectively used by adhesion of the strip 15 to the skin surfaces of the user immediately above his pubic area. Once used, the article may be conveniently discarded.

Obviously many modifications and changes may be made to the foregoing description without departing from the spirit of the invention. It is therefore intended that the scope of the invention be determined solely on the claims appended hereto.

What is claimed is:

1. A flexible shield conformed for attachment to the person of a male user, comprising:
   a resilient, thin, pliable membrane of substantially rectangular planform defined by an upper edge, and lateral edges extending therebetween;
   an adhesive strip formed on the surface of said membrane in adjacent proximity with said upper edge;
   a peelable cover releasably adhered to said strip;
   a frustoconical, tubular segment extending from said membrane proximate the center thereof defined by a peripheral wall of axially decreasing thickness towards the end opening thereof;
   a sectionally enlarged edge bead formed in said membrane at the lower edge thereof; and
   a plurality of elongate sectionally enlarged ribs formed in said membrane and aligned radially from said tubular segment toward said edges of said membrane, whereby said ribs and said edge bead cooperate to expand said membrane.

2. A shield, according to claim 1, wherein:
   the juncture between said conical segment and said membrane is formed along a toroidal surface.

* * * * *